United States Patent [19]
Jaetsch et al.

[11] Patent Number: 5,618,815
[45] Date of Patent: Apr. 8, 1997

[54] 1,9-BRIDGED THIAZOLO[3,2-A]QUINOLINE DERIVATIVES

[75] Inventors: Thomas Jaetsch, Köln; Werner Hallenbach, Monheim; Thomas Himmler, Odenthal; Burkhard Mielke, Leverkusen; Klaus D. Bremm, Recklinghausen; Rainer Endermann, Wuppertal; Franz Pirro, Langenfeld; Michael Stegemann; Heinz-Georg Wetzstein, both of Leverkusen, all of Germany

[73] Assignee: Bayer Aktiengesellschaft, Leverkusen, Germany

[21] Appl. No.: 444,246

[22] Filed: May 19, 1995

[30] Foreign Application Priority Data

May 27, 1994 [DE] Germany .......................... 44 18 510.3

[51] Int. Cl.⁶ .................. C07D 513/16; C07D 498/00; A61K 31/495; A61K 31/535
[52] U.S. Cl. .................. 514/250; 544/99; 544/105; 544/343; 514/230.5
[58] Field of Search .................. 544/343, 105, 544/99; 514/230.5, 250

[56] References Cited

U.S. PATENT DOCUMENTS

| | | | |
|---|---|---|---|
| 4,808,584 | 2/1989 | Taguchi et al. | 544/99 |
| 4,971,967 | 11/1990 | Kondo et al. | 514/250 |
| 5,166,203 | 11/1992 | Kondo et al. | 514/230.5 |
| 5,411,960 | 2/1995 | Schwenner et al. | 514/230.5 |
| 5,468,742 | 11/1995 | Petersen et al. | 544/105 |

FOREIGN PATENT DOCUMENTS

| | | |
|---|---|---|
| 0286089 | 10/1988 | European Pat. Off. |
| 0387877 | 9/1990 | European Pat. Off. |
| 0472826 | 3/1992 | European Pat. Off. |
| 0520240 | 12/1992 | European Pat. Off. |
| 0523512 | 1/1993 | European Pat. Off. |
| 0550903 | 7/1993 | European Pat. Off. |
| 0563734 | 10/1993 | European Pat. Off. |
| 0588166 | 3/1994 | European Pat. Off. |

OTHER PUBLICATIONS

Med. Chem. 1993,36,2621–2626.
Eur. J. Med. Chem. (1991) 26,889–906.
Derwent Abstract of JP 03–190,883, Aug. 20, 1991.
Derwent Abstract of JP 04–120,081, (Apr. 21, 1992).
Y. Inoue, et al., J. Med. Chem., vol. 37, pp. 586–592, (1994).
Y. Jinbo, et al., J. Med. Chem., vol. 37, pp. 2791–2796, (1994).
Y. Jinbo, et al., J. Med. Chem., vol. 36, pp. 2621–2626, (1993).

Primary Examiner—Cecilia Tsang
Assistant Examiner—Brenda Coleman
Attorney, Agent, or Firm—Sprung Horn Kramer & Woods

[57] ABSTRACT

The present invention relates to 1,9-bridged thiazolo[3,2-a] quinoline derivatives of the general formula (I)

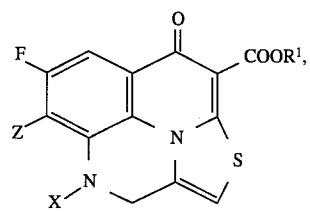

in which the substituents Z, X, R¹ have the meaning given in the description, to processes for their preparation and to their use in antibacterial compositions.

11 Claims, No Drawings

1,9-BRIDGED THIAZOLO[3,2-A]QUINOLINE DERIVATIVES

The present invention relates to 1,9-bridged thiazolo-[3,2-a]quinoline derivatives, to processes for their preparation and to antibacterial compositions containing these derivatives.

It has already been disclosed that thiaazoloquinolinecarboxylic acids are antibacterially active. Examples thereof can be found in EP-O 286 089, EP-0 387 877, EP-O 472 826 and in the Journal of Medicinal Chemistry 36, 2621 (1993).

Compounds of the general formula (I)

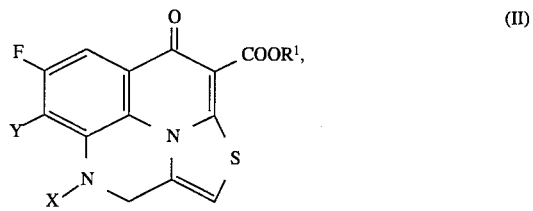
(I)

have now been found in which
$R^1$ represents hydrogen, optionally hydroxyl-, methoxy-, amino-, methylamino- or dimethylamino- substituted alkyl having 1 to 4 carbon atoms or (5-methyl-2-oxo-1,3-dioxol-4-yl)-methyl, X represents straight-chain or branched $C_1$-$C_3$-alkyl or cyclopropyl, Z represents radicals of the structures

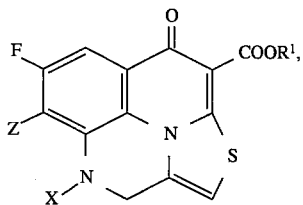

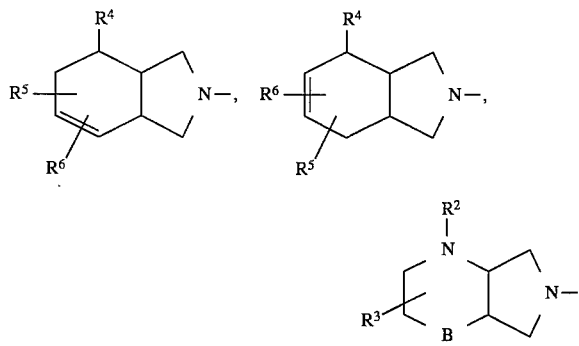

in which
$R^4$ represents hydrogen, hydroxyl, -$NR^7R^8$, hydroxymethyl, —$CH_2$—$NR^7R^8$, carboxyl, methoxycarbonyl or ethoxycarbonyl, where
  $R^7$ represents hydrogen, optionally hydroxyl-substituted $C_1$-$C_3$-alkyl, alkoxycarbonyl having 1 to 4 carbon atoms in the alkoxy moiety or $C_1$-$C_3$-acyl,
  $R^8$ represents hydrogen or methyl,
$R^5$ represents hydrogen, straight-chain or branched $C_1$-$C_3$-alkyl or cyclopropyl,
$R^6$ represents hydrogen or methyl,
$R^3$ represents hydrogen or methyl,
$R^2$ represents hydrogen, methyl or radicals of the structures —CH=CH—$COOR^{2'}$, —$CH_2$—$CH_2$—$COOR^{2'}$, —$CH_2$—CO—$CH_3$, —$CH_2$—$CH_2$—CN,
$R^{2'}$ represents methyl or ethyl,
B represents —$CH_2$—, O or a direct bond.

The compounds of the formula (I) may be present in the form of racemates or as enantiomerically pure compounds and also in the form of their pharmaceutically utilizable hydrates and acid addition salts, and in the form of their alkali metal, alkaline earth metal, silver or guanidinium salts.

The compounds of the formula (I) are obtained of compounds of the formula (II)

(II)

in which
$R^1$ and X have the meaning given above and
Y represents fluorine or chlorine, are reacted with compounds of the formula (III)

Z—H (III)

in which
Z has the meaning given above, if desired in the presence of acid scavengers.

In comparison with known representatives of this structural type, the compounds according to the invention have a higher antibacterial action, especially in the Gram-positive region. They are therefore suitable as active compounds for human and veterinary medicine.

Preferred compounds of the formula (I) are those in which
$R^1$ represents hydrogen, optionally hydroxyl-, methoxy-, amino-, methylamino- or dimethylamino- substituted alkyl having 1 to 4carbon atoms or (5-methyl-2-oxo-1,3-dioxol-4-yl)-methyl, X represents methyl, ethyl or cyclopropyl, Z represents radicals of the structures

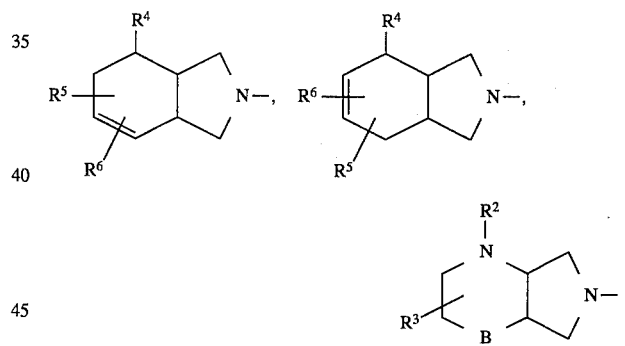

in which
$R^4$ represents hydrogen, hydroxyl, -$NR^7R^8$, hydroxymethyl, —$CH_2$—$NR^7R^8$, where
  $R^7$ represents hydrogen, optionally hydroxyl-substituted $C_1$-$C_2$-alkyl, alkoxycarbonyl having 1 to 4 carbon atoms in the alkoxy moiety or $C_1$-$C_3$-acyl,
  $R^8$ represents hydrogen or methyl,
$R^5$ represents hydrogen, straight-chain or branched $C_1$-$C_3$-alkyl or cyclopropyl,
$R^6$ represents hydrogen or methyl,
$R^3$ represents hydrogen,
$R^2$ represents hydrogen or methyl,
B represents —$CH_2$—, O or a direct bond,
and their pharmaceutically utilizable hydrates and acid addition salts, and the alkali metal, alkaline earth metal, silver and guanidinium salts of the carboxylic acids on which they are based.

Particularly preferred compounds of the formula (I) are those in which $R^1$ represents hydrogen, methyl or ethyl, X represents methyl or ethyl, Z represents radicals of the structures

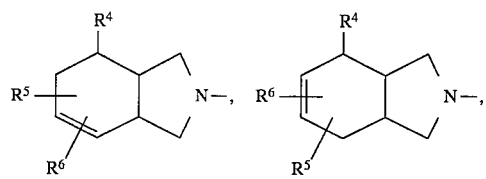

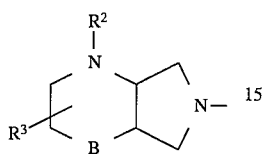

in which $R^4$ represents hydrogen, hydroxyl, -NR$^7$R$^8$, hydroxymethyl, —CH$_2$—NR$^7$R$^8$, where $R^7$ represents hydrogen, methyl, alkoxycarbonyl having 1 to 4 carbon atoms in the alkoxy moiety or $C_1$-$C_3$-acyl, $R^8$ represents hydrogen or methyl, $R^5$ represents hydrogen, straight-chain or branched $C_1$-$C_3$-alkyl or cyclopropyl, $R^6$ represents hydrogen or methyl, $R^3$ represents hydrogen, $R^2$ represents hydrogen or methyl, B represents —CH$_2$—, O or a direct bond, and their pharmaceutically utilizable hydrates and acid addition salts, and the alkali metal, alkaline earth metal, silver and guanidium salts of the carboxylic acids on which they are based.

The following compounds of the formula (I) are listed below:

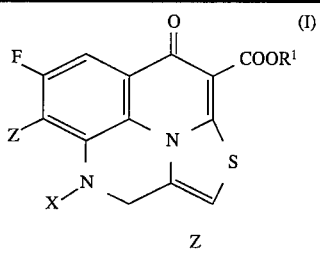

| X | R$^1$ | Z |
|---|---|---|
| cyclopropyl | H | 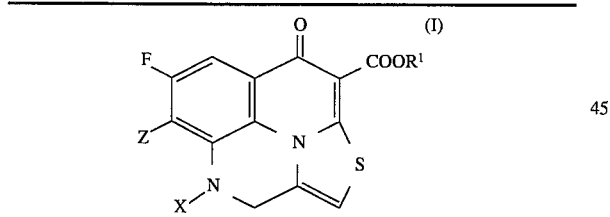 |
| Me | H | 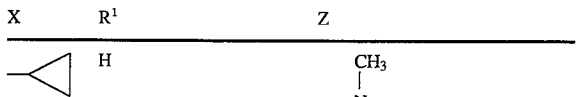 |
| Me | Et | 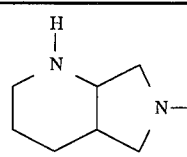 |
| cyclopropyl | H | 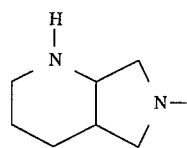 |
| cyclopropyl | H | 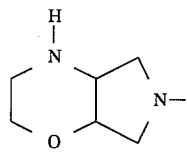 |
| Et | H | 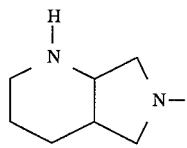 |
| cyclopropyl | H | 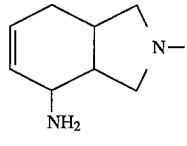 |
| Me | Ethyl | 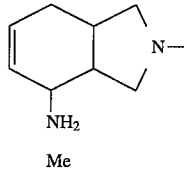 |
| Me | H | 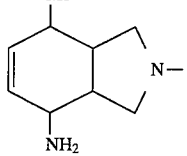 |
| cyclopropyl | H | 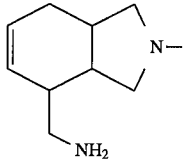 |

5 -continued
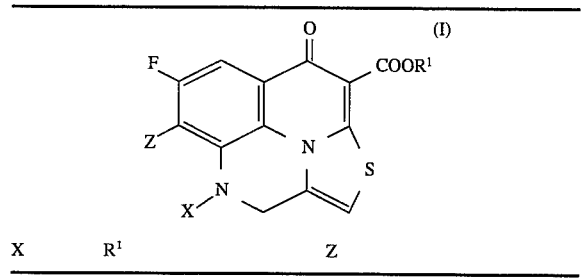
| X | R¹ | Z |
|---|---|---|
| cyclopropyl | Ethyl | 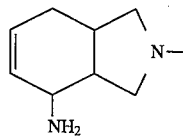 |
| Me | —CH₂—CH₂—NH₂ | 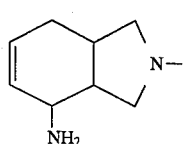 |
| Me | —CH₂—CH₂—OCH₃ | 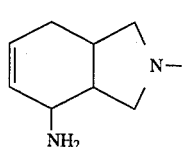 |
| cyclopropyl | H | 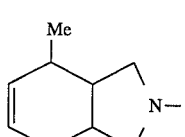 |
| Et | H | 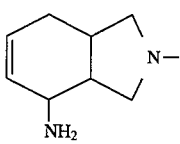 |
| Et | Ethyl | |
| cyclopropyl | —CH₂—CH₂—NH₂ | 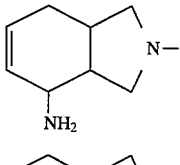 |
| cyclopropyl | —CH₂—CH₂—OCH₃ | 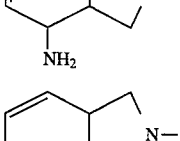 |
| Me | Ethyl | 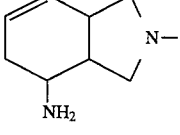 |
6 -continued
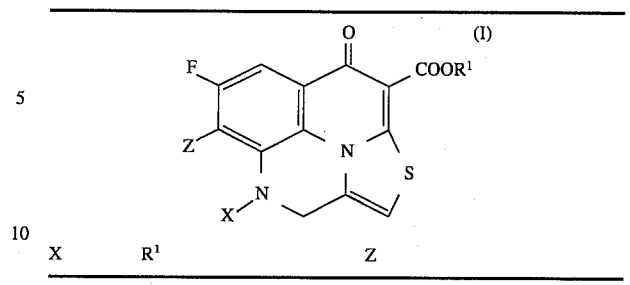
| X | R¹ | Z |
|---|---|---|
| cyclopropyl | H | 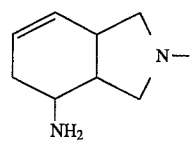 |
| Et | H | 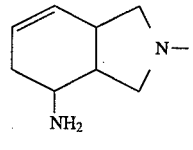 |
| Et | H | 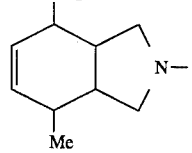 |
| Me | H | 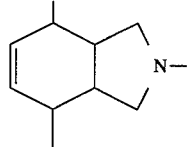 |
| cyclopropyl | H | 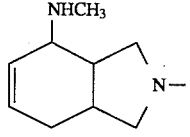 |
| Et | H | 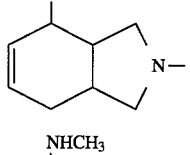 |
| cyclopropyl | H | 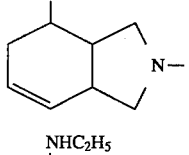 |
| Me | H | 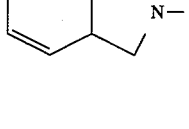 |

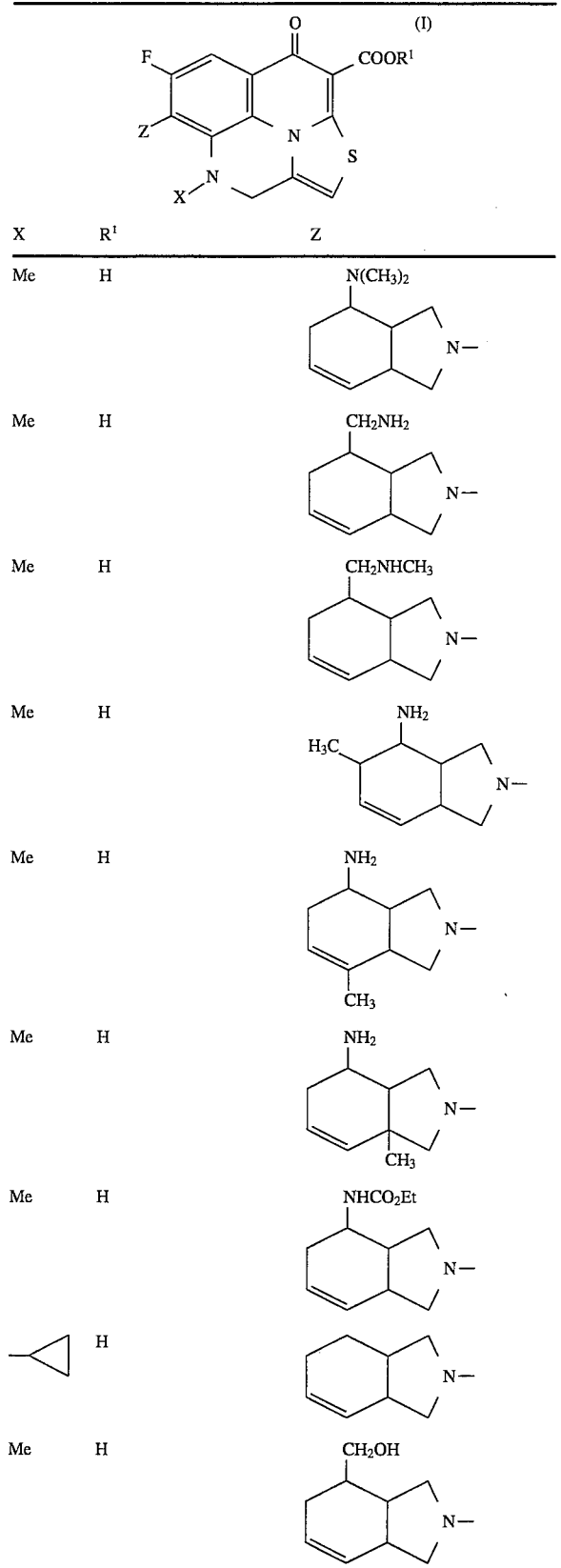

Using, for example, 7,8-difluoro-5-oxo-9,1-([N-methylimino)methan]-5H-thiazolo[3,2-a]quinoline-4-carboxylic acid and 2,8-diazabicyclo[4.3.0]nonane for the preparation of compounds of the formula (I), the course of the reaction can be reproduced by the following equation:

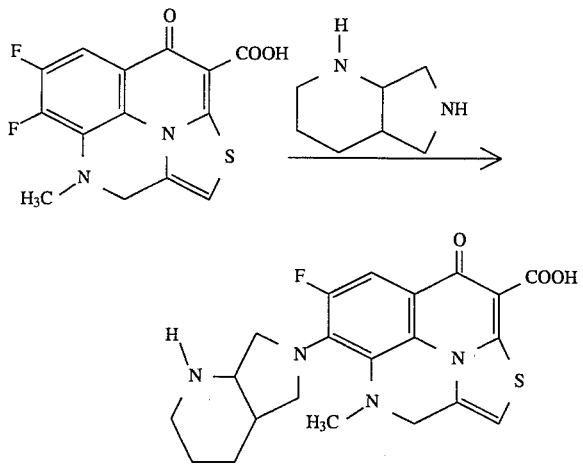

The compounds of the formula (II) which are used as starting compounds are known and/or can be prepared by known methods. They may if desired be employed as racemates, enantiomers or pure diastereomers.

Examples which may be mentioned are:

7,8-Difluoro-5-oxo-9,1-[(N-methylimino)methano]-5H-thiazolo[3,2-a]quinoline-4-carboxylic acid 7,8-Difluoro-5-oxo-9,1-[(N-ethylimino)methano]-5H-thiazolo[3,2-a]quinoline-4-carboxylic acid 7,8-Difluoro-5-oxo-9,1-[(N-cyclopropylimino)methano]-5H-thiazolo[3,2-a]quinoline-4-carboxylic acid Ethyl 7,8-difluoro-5-oxo-9,1-[(N-methylimino) methano]-5H-thiazolo[3,2-a]quinoline-4-carboxylate Ethyl 7,8-difluoro-5-oxo-9,1-[(N-ethylimino)methano]-5H-thiazolo[3,2-a]quinoline-4-carboxylate The amines of the formula (III) which are used as starting compounds are known. Chiral amines can be employed not only as racemates but also as enantiomerically pure or diastereomerically pure compounds.

Examples which may be mentioned are:

2,7-Diazabicyclo[3.3.0]octane

2-Methyl-2,7-diazabicyclo[3.3.0]octane 2,8-Diazabicyclo[4.3.0]nonane

2-Methyl -2,8-diazabicyclo[4.3.0]nonane

2-Oxa-5,8-diazabicyclo[4.3.0]nonane

5-Methyl-2-oxa-5,8-diazabicyclo[4.3.0]nonane.

2-Amino- 8-azabicyclo[4.3.0]non-3-ene

2-Methylamino-8-azabicyclo[4.3.0]non-3-ene

4-Methyl-2-methylamino-8-azabicyclo[4.3.0]non-3-ene

5-Methyl-2-methylamino-8-azabicyclo[4.3.0]non-3-ene

2-Dimethylamino-8-azabicyclo[4.3.0]non-3-ene

2-Ethylamino-8-azabicyclo[4.3.0]non-3-ene

2-Methylaminomethyl-8-azabicyclo[4.3.0]non-3-ene

2-Hydroxy-8-azabicyclo[4.3.0]non-3-ene

5-Isopropyl-2-methylamino-8-azabicyclo[4.3.0]non-3-ene

2-Amino-5-isopropyl-8-azabicyclo[4.3.0]non-3-ene

2-Amino-5-methyl-8-azabicyclo[4.3.0]non-3-ene

2-Hydroxymethyl-8-azabicyclo[4.3.0]non-3-ene

2-Amino-5-cyclopropyl-8-azabicyclo[4.3.0]non-3-ene

8-Azabicyclo[4.3.0]non-2-ene

Ethyl 8-azabicyclo[4.3.0]non-4-ene-2-carboxylate

2-Hydroxymethyl-8-azabicyclo[4.3.0]non-4-ene

2-Amino-8-azabicyclo[4.3.0]non-4-ene

2-Ethyloxycarbonylamino-8-azabicyclo[4.3.0]non-4-ene 2-tert-Butyloxycarbonylamino-8-azabicyclo[4.3.0]non-4-ene 2-Benzyloxycarbonylamino-8-azabicyclo[4.3.0]non-4-ene 2- Allyloxycarbonylaminomethyl-8-azabicyclo[4.3.0]non-4-ene 2-Aminomethyl-8-azabicyclo[4.3.0]non-4-ene 2-Ethyloxycarbonylaminomethyl-8-azabicyclo[4.3.0]non-4-ene 2-tert-Butyloxycarbonylaminomethyl-8-azabicyclo[4.3.0]-non-4-ene 2-Methylamino-8-azabicyclo[4.3.0]non-4-ene 2-Ethylamino-8-azabicyclo[4.3.0]non-4-ene 2-Cyclopropylamino-8-azabicyclo[4.3.0]non-4-ene 2-Dimethylamino-8-azabicyclo[4.3.0]non-4-ene 2-[(2-Hydroxyethyl)-amino]-8-azabicyclo[4.3.0]non-4-ene 2-Amino-1-methyl-8-azabicyclo[4.3.0]non-4-ene 2-Amino-2-methyl-8-azabicyclo[4.3.0]non-4-ene 2-Amino-3-methyl-8-azabicyclo[4.3.0]non-4-ene 2-Ethyloxycarbonylamino-3-methyl-8-azabicyclo[4.3.0]non-4-ene 2-tert-Butyloxycarbonylamino-3-methyl-8-azabicyclo-4.3.0]non-4-ene 2-Benzyloxycarbonylamino-3-methyl-8-azabicyclo[4.3.0]non-4-ene 2-Allyloxycarbonylaminomethyl-3-methyl-8-azabicyclo-[4.3.0]non-4-ene 2-Amino-4-methyl-8-azabicyclo[4.3.0]non-4-ene 2-Amino-5-methyl-8-azabicyclo[4.3.0]non-4-ene 2-Amino-6-methyl-8-azabicyclo[4.3.0]non-4-ene 2-Amino-7-methyl-8-azabicyclo[4.3.0]non-4-ene 2-Amino-9-methyl-8-azabicyclo[4.3.0]non-4-ene The reaction of (II) with (III), in which the compounds (III) may also be employed in the form of their salts, for example the hydrochlorides, is preferably carried out in a diluent such as dimethyl sulphoxide, N,N-dimethylformamide, N-methylpyrrolidone, hexamethyl-phosphoric trisamide, sulpholane, acetonitrile, water, an alcohol such as methanol, ethanol, n-propanol, isopropanol, glycol monomethyl ether, or pyridine. Mixtures of these diluents may also be used.

All conventional inorganic and organic acid-binding agents can be used as acid binders. These include, preferably, the alkali metal hydroxides, alkali metal carbonates, organic amines and amidines. Specific compounds which are particularly suitable are: triethylamine, 1,4-diazabicyclo [2.2.2]octane (DABCO), 1,8-diazabicyclo-[5.4.0]undec-7-ene (DBU) or excess amine (III).

The reaction temperatures can be varied over a relatively wide range. The reaction is in general carried out at between about 20° and 200° C., preferably between 80° and 180° C.

The reaction can be carried out either at atmospheric pressure or at elevated pressure. It is generally carried out at pressures of between 1 bar and 100 bar, preferably between 1 and 10 bar.

When carrying out the process according to the invention, from 1 to 15 mol, preferably from 1 to 6 mol, of the compound (III) are employed per mole of the compound II.

Free amino Groups may be protected during reaction by a suitable amino-protecting group, for example by the tert-butoxycarbonyl radical, and can be liberated again at the end of the reaction by treatment with a suitable acid, such as hydrochloric acid or trifluoroacetic acid (see Houben-Weyl, Methoden der Organischen Chemie [Methods of Organic Chemistry], Volume E4, page 144 (1983); J. F. W. McOmie, Protective Groups in Organic Chemistry (1973), page 43).

The esters according to the invention are obtained by reacting an alkali metal salt of the carboxylic acid on which they are based, which may if desired be protected at the N atom by a protective Group such as the tert-butoxycarbonyl radical, with appropriate halogenoalkyl derivatives in a solvent such as dimethylformamide, dimethylacetamide, N-methylpyrrolidone, dimethyl sulphoxide or tetramethylurea at temperatures from about 0° to 100° C., preferably from 0° to 50° C.

The acid addition salts of the compounds according to the invention are prepared in a conventional manner, for example by dissolving the betaine in a sufficient quantity of aqueous acid and precipitating the salt with a water-miscible organic solvent such as methanol, ethanol, acetone, acetonitrile. It is also possible to heat equivalent quantities of betaine and acid in water or in an alcohol such as glycol monoethyl ether, and then to evaporate the mixture to dryness or filter off the precipitated salt with suction. Pharmaceutically utilizable salts are to be understood, for example, as the salts of hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic sows, embonic acid, glutamic acid or aspartic acid. Furthermore, the compounds according to the invention can be bound on acid or basic ion exchangers.

The alkali metal or alkaline earth metal salts of the carboxylic acids according to the invention are obtained, for example, by dissolving the betaine in a less than equivalent quantity of alkali metal or alkaline earth metal hydroxide solution, filtering to remove undissolved betaine, and evaporation of the filtrate to dryness. Pharmaceutically suitable salts are sodium, potassium or calcium salts. The corresponding silver salts are obtained by reaction of an alkali metal salt or alkaline earth metal salt with an appropriate silver salt, such as silver nitrate.

The compounds according to the invention have a strong antibiotic action and combine low toxicity with a broad antibacterial spectrum against Gram-positive and Gram-negative microorganisms, including in particular those which are resistant to various antibiotics such as, for example, penicillins, cephalosporins, aminoglycosides, sulphonamides, tetracyclines.

These valuable properties make it possible for them to be used as chemotherapeutic active compounds in human and veterinary medicine and as substances for preserving inorganic and organic materials, especially organic materials of all kinds, for example polymers, lubricants, paints, fibres, leather, paper and wood, foodstuffs and water.

The compounds according to the invention are effective against a very broad spectrum of microorganisms. They can be used to control Gram-negative and Gram-positive bacteria and bacteria-like microorganisms, as well as to prevent, ameliorate and/or cure the diseases caused by these pathogens.

The compounds according to the invention are distinguished by an amplified effect on dormant and resistant microorganisms. In the case of dormant bacteria, that is bacteria which show no detectable growth, the compounds are active at concentrations below those of similar substances. This relates not only to the quantity to be employed but also to the rate of destruction. Results of this kind have been observed for Gram-positive and Gram-negative bacteria, in particular for *Staphylococcus aureus, Micrococus luteus* and *Enterococcus faecalis*.

The compounds according to the invention also exhibit surprising increases in action against bacteria which are categorized as being less sensitive towards comparable substances, especially resistant *Staphylococcus aureus* and *Enterococcus faecalis*.

The compounds according to the invention are particularly effective against bacteria and bacteria-like microorganisms. They are therefore particularly well suited to the prophylaxis and chemotherapy of local and systemic infections which are caused by these pathogens in human and veterinary medicine.

The compounds are also suitable for controlling diseases caused by protozoa and helminths.

The compounds according to the invention can be used in various pharmaceutical preparations. Preferred pharmaceutical preparations which may be mentioned are tablets, coated tablets, capsules, pills, granules, suppositories, solutions for injection and solutions which can be administered orally, suspensions and emulsions, and also pastes, ointments, gels, creams, lotions, powders and sprays.

While remaining of favourable toxicity to warm-blooded creatures, the active compounds are preferably suitable for controlling bacterial diseases which are encountered in the keeping and breeding of livestock, breeding stock, zoo animals, laboratory animals, experimental animals and pets. In this context they are active against all or individual stages of development and against resistant and normally sensitive strains. By combating the bacterial diseases the intention is to reduce disease, fatalities and reductions in yield (for example in the production of meat, milk, wool, skins, eggs, honey and the like), so that the use of the active compounds enables the keeping of animals to be more economic and of greater simplicity.

The livestock and breeding stock include mammals, such as, for example, cattle, horses, sheep, pigs, goats, camels, water buffalo, donkeys, rabbits, fallow deer, reindeer, fur-bearing animals such as, for example, mink, chinchilla, raccoon, birds such as, for example, chickens, geese, turkeys, ducks, doves, and species of birds which are kept domestically and in zoos. They also include economically useful fish and aquarium fish.

The laboratory and experimental animals include mice, rats, guinea pigs, golden hamsters, dogs and cats.

The pets include dogs and cats.

The fish include economically useful fish, cultured fish, aquarium fish and decorative fish of all ages which live in fresh water and sea water. The economically useful fish and cultured fish include, for example, carp, eel, trout, whitefish, salmon, bream, roach, rudd, dobule, sole, plaice, halibut, Japanese yellowtail (*Seriola quinqueradiata*), Japanese eel (*Anguilla japonica*), red sea bream (*Pagurus major*), sea bass (*Dicentrarchus labrax*), grey mullet (*Mugilus cephalus*), pompano, giltbread sea bream (*Sparus auratus*), *Tilapia spp.*, Chichlidae species such as, for example, Plagioscion, Channel catfish. The compositions according to the invention are particularly suitable for treating fish fry, for example carps of 2–4 cm in body length. The compositions are also highly suitable in eel fattening.

Administration can be effected prophylactically as well as therapeutically.

The active substances are administered directly or in the form of suitable preparations, enterally, parenterally, dermally, nasally.

Enteral administration of the active compounds is effected, for example, orally in the form of powders, suppositories, tablets, capsules, pastes, drinks, granules, drenches, boli, medicated feed or drinking water. Dermal application is effected, for example, in the form of dipping, spraying, bathing, washing, pouring-on and spotting-on, and powdering. Parenteral administration is effected, for example, in the form of injection (intramuscular, subcutaneous, intravenous or intraperitoneal) or by implants.

The following are suitable preparations:

solutions, such as solutions for injection, oral solutions, concentrates for oral administration after dilution, solutions for use on the skin or in body cavities, pour-on formulations, gels;

emulsions and suspension for oral or dermal administration and for injection; semi-solid preparations;

formulations in which the active compound is incorporated in an ointment base or in an oil-in-water or water-in-oil emulsion base;

Solid preparations, such as powders, premixes or concentrates, granules, pellets, tablets, boli, capsules; aerosols and inhalants, shaped articles containing active compound.

Solutions for injection are administered intravenously, intramuscularly and subcutaneously.

Solutions for injection are prepared by dissolving the active compound in a suitable solvent and, if desired, adding additives, such as solubilizers, acids, bases, buffer salts, antioxidants, preservatives. The solutions are sterile-filtered and dispensed into containers.

The following may be mentioned as solvents: physiologically compatible solvents, such as water, alcohols, such as ethanol, butanol, benzyl acohol, glycerol, hydrocarbons, propylene glycol, polyethylene glycols, N-methylpyrrolidone, and their mixtures.

If appropriate, the active compounds can also be dissolved in physiologically compatible vegetable or synthetic oils which are suitable for injection.

The following may be mentioned as solubilizers: solvents which facilitate the dissolution of the active compound in the main solvent or which prevent precipitation of the active compound. Examples are polyvinylpyrrolidone, polyoxyethylated castor oil and polyoxyethylated sorbitan esters.

The following are preservatives: benzyl alcohol, trichlorobutanol, p-hydroxybenzoic esters, n-butanol.

Oral solutions are administered directly. Concentrates are first diluted to the administration concentration and then administered orally. Oral solutions and concentrates are prepared as described above in the case of the solutions for injection, sterile procedures not being necessary.

Solutions for use on the skin are applied drop by drop, smoothed on, rubbed in, splashed on, sprayed on or applied by dipping, bathing or washing. These solutions are prepared as described above in the case of the solutions for injection.

It may be advantageous to add thickeners in the preparation process. The following are thickeners: inorganic thickeners, such as bentonites, colloidal silica, aluminum monostearate, organic thickeners, such as cellulose derivatives, polyvinyl alcohols and their copolymers, acrylates and metacrylates.

Gels are applied to the skin or smoothed on or introduced into body cavities. Gels are prepared by adding, to solutions which have been prepared as described for the solutions for injection, an amount of thickener such that a clear composition is formed which has an ointment-like consistency. The thickeners used are the thickeners indicated further above.

Pour-on and spot-on formulations are poured or splashed onto defined areas of the skin, the active compound either penetrating the skin and acting systemically or being distributed on the surface of the body.

Pour-on and spot-on formulations are prepared by dissolving, suspending or emulsifying the active compound in suitable solvents or solvent mixtures which are tolerated by the skin. If appropriate, other auxiliaries are added, such as colourants, absorption accelerators, antioxidants, light stabilizers, tackifiers.

The following may be mentioned as solvents: water, alkanols, glycols, polyethylene glycols, polypropylene glycols, glycerol, aromatic alcohols, such as benzyl alcohol, phenylethanol or phenoxyethanol, esters, such as ethyl acetate, butyl acetate or benzyl benzoate, ethers, such as alkylene glycol alkyl ethers, such as dipropylene glycol monomethyl ether or diethylene glycol mono-butyl ether, ketones, such as acetone or methyl ethyl ketone, aromatic and/or aliphatic hydrocarbons, vegetable or synthetic oils, DMF, dimethylacetamide, N-methyl-pyrrolidone, or 2-dimethyl-4-oxy-methylene-1,3-dioxolane.

Colourants are all colourants which can be dissolved or suspended and which are approved for use in animals.

Examples of absorption accelerators are DMSO, spreading oils, such as isopropyl myristate, dipropylene glycol pelargonate, silicone oils, fatty acid esters, triglycerides or fatty alcohols.

The following are antioxidants: sulphites or metabisulphites, such as potassium metabisulphite, ascorbic acid, butylhydroxytoluene, butylhydroxyanisole or tocopherol.

Examples of light stabilizers are substances from the class of the benzophenones, or novantisolic acid.

Tackifiers are, for example, cellulose derivatives, starch derivatives, polyacrylates or natural polymers such as alginates or gelatine.

Emulsions can be administered orally, dermally or as injections.

Emulsions are either of the water-in-oil type or of the oil-in-water type.

They are prepared by dissolving the active compound either in the hydrophobic or in the hydrophilic phase and by homogenizing this phase with the solvent of the other phase, with the aid of suitable emulsifiers and, if appropriate, other auxiliaries, such as colourants, absorption accelerators, preservatives, antioxidants, light stabilizers and viscosity-increasing substances.

The following may be mentioned as the hydrophobic phase (oils): paraffin oils, silicone oils, natural vegetable oils such as sesame seed oil, almond oil or castor oil, synthetic triglycerides, such as caprylic/capric acid bigylceride, a triglyceride mixture with vegetable fatty acids of chain length $C_{8-12}$ or other specifically selected natural fatty acids, mixtures of partial glycerides of saturated or unsaturated fatty acids which may also contain hydroxyl groups, and mono- and diglycerides of the $C_8/C_{10}$ fatty acids.

Fatty acid esters, such as ethyl stearate, di-n-butyryladipate, hexyl laurate, dipropylene glycol pelargonate, esters of a branched fatty acid having a medium chain length with saturated fatty alcohols of chain length $C_{16}$–$C_{18}$, isopropyl myristate, isopropyl palmitate, caprylic/capric esters of saturated fatty alcohols of chain length $C_{12}$–$C_{18}$, isopropyl stearate, oleyl oleate, decyl oleate, ethyl oleate, ethyl lactate, waxy fatty acid esters such as dibutyl phthalate, diisopropyl adipate, ester mixtures related to the latter, and other fatty alcohols, such as isotridecyl alcohol, 2-octyldodecanol, cetylstearyl alcohol or oleyl alcohol.

Fatty acids such as, for example, oleic acid and its mixtures.

The following may be mentioned as the hydrophilic phase: water, alcohols, such as; for example, propylene glycol, glycerol, sorbitol and their mixtures.

The following may be mentioned as emulsifiers: non-ionic surfactants, for example polyoxyethylated castor oil, polyoxyethylated sorbitan monooleate, sorbitan monostearate, glycerol monostearate, polyoxyethyl stearate or alkylphenol polyglycol ethers;

ampholytic surfactants, such as di-Na-N-lauryl-β-iminodipropionate or lecithin;

anionic surfactants, such as Na lauryl sulphate, fatty alcohol ether sulphates, and the monoethanolamine salt of mono/dialkylpolyglycol ether orthophosphoric esters;

cationic surfactants, such as cetyltrimethylammonium chloride.

The following may be mentioned as other auxiliaries: substances which increase the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, methyl vinyl ether/maleic anhydride copolymers, polyethylene glycols, waxes, colloidal silica, or mixtures of the listed substances.

Suspensions can be administered orally, dermally or as an injection. They are prepared by suspending the active compound in a liquid excipient, if appropriate with the addition of other auxiliaries, such as wetting agents, colourants, absorption accelerators, preservatives, antioxidants light stabilizers.

Liquid excipients which may be mentioned are all homogeneous solvents and solvent mixtures.

Wetting agents (dispersants) which may be mentioned are the surfactants indicated further above.

Other auxiliaries which may be mentioned are those indicated further above.

Semi-solid preparations can be administered orally or dermally. They are only distinguished from the above-described suspensions and emulsions by their higher viscosity.

To prepare solid preparations, the active compound is mixed with suitable excipients, if appropriate with the addition of auxiliaries, and the mixture is formulated as desired.

Excipients which may be mentioned are all physiologically compatible solid inert substances. Suitable for this purpose are inorganic and organic substances. Inorganic substances are, for example, common salt, carbonates, such as calcium carbonate, hydrogen carbonates, aluminium oxides, silicas, clays, precipitated or colloidal silicon dioxide, and phosphates.

Organic substances are, for example, sugars, cellulose, foodstuffs and animal feeds, such as powdered milk, animal meals, cereal meals, coarse cereal meals and starches.

Auxiliaries are preservatives, antioxidants and colourants which have already been mentioned further above.

Other suitable auxiliaries are lubricants and gliding agents, such as, for example, magnesium stearate, stearic acid, talc, bentonites, disintegrants, such as starch or crosslinked polyvinylpyrrolidone, binders such as, for example, starch, gelatin or linear polyvinylpyrrolidone, and dry binders, such as microcrystalline cellulose.

In the preparations, the active compounds can also be present as a mixture with synergists or with other active compounds.

Ready-to-use preparations contain the active compound in concentrations of 10 ppm to 20 percent by weight, preferably from 0.1 to 10 percent by weight.

Preparations which are diluted before use contain the active compound in concentrations of 0.5 to 90 percent by weight, preferably from 1 to 50 percent by weight.

In general, it has proved advantageous to administer amounts of about 0.5 to about 50 mg, preferably from 1 to 20 mg, of active compound per kg of body weight per day, to achieve effective results.

The active compounds may also be administered together with the feed or drinking water of the animals.

Feedstuffs and nutrients contain from 0.01 to 100 ppm, preferably from 0.5 to 50 ppm, of the active compound in combination with a suitable, edible material.

A feedstuff and nutrient of this kind can be used both for curative purposes and for prophylactic purposes.

A feedstuff or nutrient of this kind is prepared by mixing a concentrate or a premix containing from 0.5 to 30%, preferably from 1 to 20% by weight, of an active compound, in a mixture with an edible organic or inorganic excipient, with conventional feedstuffs. Examples of edible excipients are cornflour or corn and soya-bean flour, or mineral salts, which preferably contain a small quantity of an edible anti-dust oil, for example corn oil or soya oil. The resulting premix can then be added to the complete feedstuff before it is fed to the animals.

The minimum inhibitory concentrations (MICs) of the compounds according to the invention were determined by serial dilution methods on Iso-Sensitest agar (Oxoid). For each test substance a series of agar plates was, prepared, which plates contained decreasing concentrations of the active compound, with twofold dilution in each case. The agar plates were inoculated with a Multipoint inoculator (Denley). Inoculation was carried out using overnight cultures of the pathogens, which had been diluted beforehand so that each inoculation point contained about $10^4$ colony-forming particles. The inoculated agar plates were incubated at 37° C., and the growth of the microorganisms was read off after about 20 hours. The MIC (µg/ml) indicates the lowest concentration of active compound at which no growth-could be perceived with the naked eye.

In the table below, the MICs of some of the compounds according to the invention are listed.

TABLE

| | | MIC values | | |
| | | Example No. | | |
| Species | Strain | 3 | 5 | 7 |
| --- | --- | --- | --- | --- |
| Staphylococcus aureus | ATCC 29123 | ≦0.015 | ≦0.015 | ≦0.015 |
| | 133 | ≦0.015 | ≦0.015 | ≦0.015 |
| | ICB 25701 | 0.125 | 0.125 | 0.25 |
| | ICB 25768 | 0.25 | 0.5 | 1 |
| Enterococcus faecalis | 27 101 | 0.125 | 0.062 | 0.126 |
| | 9790 | 0.125 | 0.062 | 0.125 |
| Micrococcus luteus | 9341 | 0.125 | 0.062 | 0.25 |

PREPARATION OF THE ACTIVE COMPOUNDS

Example 1

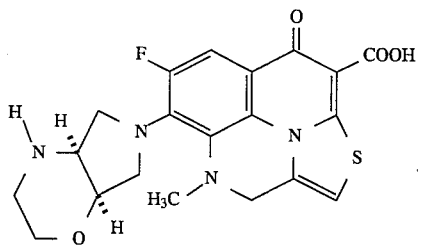

7-Fluoro-8-(1R,6S)-2-oxa-5,8-diazabicyclo[4.3.0]
nonan-8-yl)-5-oxo-9,1-[(N-methylimino)methano]-
5H-thiazolo[3,2a]quinoline-4-carboxylic acid 150 mg (0.0465 mmol) of 7,8-difluoro-5-oxo-9,1-[(N-methylimino)methano]-5H-thiazolo[3,2-a]-quinoline4-carboxylic acid are heated under argon at 120° to 130° C. for three hours with 119 mg (0.93 mmool) of (IR,6S)-2-oxa-5,8-diazabicyclo-[4.3.0]nonane in 3 ml of dimethyl sulphoxide. The mixture is concentrated under a high vacuum and the residue is recrystallized from ethanol and dried.
Yield: 149 mg (74% of theory)
Melting point: >300° C.

Example 2

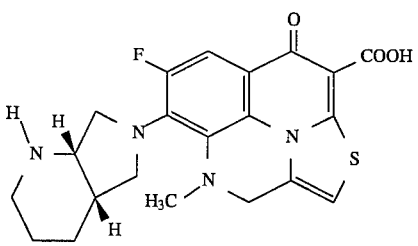

8-(1S,6S)-2,8-Diazabicyclo[4.3.0]nonan-8-yl)-7-
fluoro-5-oxo-9,1-[(N-methylimino)-methano]-5H-
thiazolo[3,2-a]-quinoline-4-carboxylic acid Analogously to Example 1, in the reaction with (1S,6S)-2,8-diazabicyclo[4.3.0]nonane, the title compound is obtained.
Melting point: 286° C. (with decomposition)

Example 3

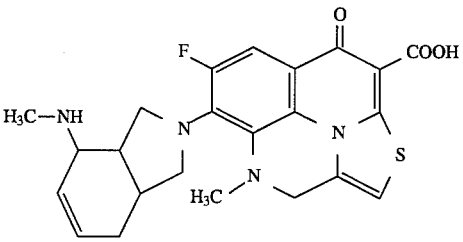

7-Fluoro-8-(2-methylamino-8-azabicyclo[4.3.0]non-
3-en-8-yl)-5-oxo-9,1-[(N-methylimino)-methano]-
5H-thiazolo-[3,2-a]quinoline-4-carboxylic acid Analogously to Example 1, in the reaction with 2-methylamino-8-azabicyclo[4.3.0]non-3-ene, the title compound is obtained.
Melting point: 228° C. (with decomposition)

Example 4

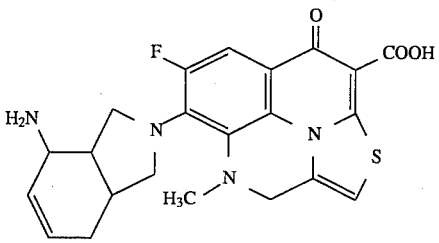

8-(2-Amino-8-azabicyclo[4.3.0]non-3-en-8-yl)-7-
fluoro-5-oxo-9,1-[(N-methylimino)-methano]-5H-
thiazolo[3,2-a]-quinoline-4-carboxylic acid Analogously to Example 1, in the reaction with 2-amino-8-azabicyclo[4,3.0]non-3-ene, the title compound is obtained.
Melting point: >300° C.

Example 5

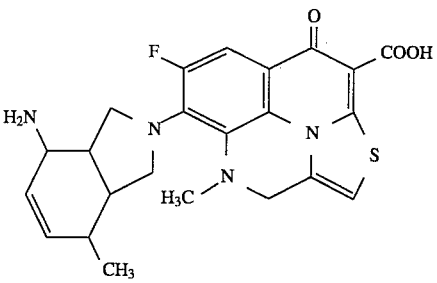

8-(2-Amino-5-methyl-8-azabicyclo[4.3.0]non-3-en-
8-yl)-7-fluoro-5-oxo-9,1-[(N-methylimino)methano]
-5H-thiazolo-[3,2-a]quinoline-4-carboxylic acid Analogously to Example 1, in the reaction with 2-amino-5-methyl-8-azabicyclo[4.3.0]non-3-ene, the title compound is obtained.
Melting point: >300° C.

Example 6

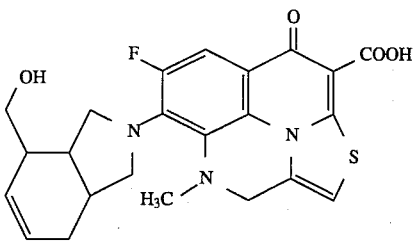

7-Fluoro-8-(2-hydroxymethyl-8-azabicyclo[4.3.0]
non-3-en-8-yl)-5-oxo-9,1-[(N-methylimino)-
methano]-5H-thiazolo-[3,2-a]quinoline-4-carboxylic
acid Analogously to Example 1, in the reaction with 2-hydroxymethyl-8-azabicyclo[4.3.0]non-3-ene, the title compound is obtained.
Melting point: >300° C.

Example 7

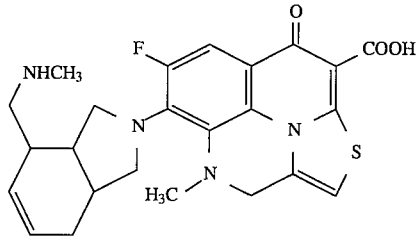

7-Fluoro-8-(2-methylamonomethyl-8-azabicyclo
[4.3.0]non-3-en-8-yl)-5-oxo-9,1-[(N-methylimino)-
methano]-5H-thiazolo-[3,2-a]quinoline-4-carboxylic
acid Analogously to Example 1, in the reaction with 2-methylaminomethyl-8-azabicyclo[4.3.0]non-3-ene, the title compound is obtained.
Melting point: 210° to 220° C. (with decomposition)

Example 8

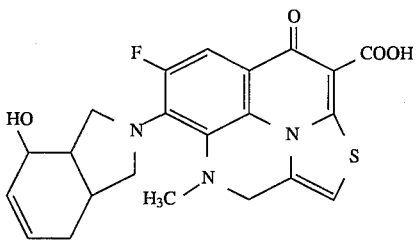

7-Fluoro-8-(2-hydroxy-8-azabicyclo[4.3.0]non-3-en-
8-yl)-5-oxo-9,1-[N-methylimino)-methano]-5H-
thiazolo[3,2-a]quinoline-4-carboxylic acid 150 mg (0.465 mmol) of 7,8-difluoro-5-oxo-9,1-[(N-methylimino)methano]-5H-thiazolo[3,2-a]quinoline-4-carboxylic acid are heated under argon at 130° C. for 9 hours with 130 mg (0.93 mmol) of 2-hydroxy-8-azabicyclo[4.3.0]non-3-ene in 3 ml of DMSO. The mixture is concentrated under a high vacuum and the residue is recrystallized from ethanol and dried.
Yield: 118 mg (57% of theory)
Melting point: 210° to 240° C. (with decomposition)

Example 9

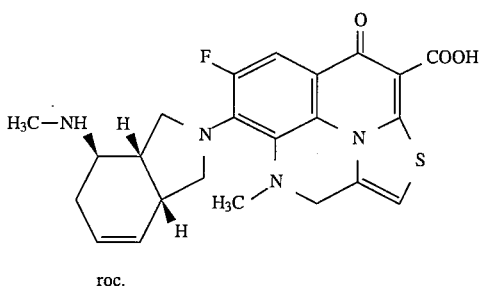

roc.

7-Fluoro-8-(1SR,2RS,6RS)-2-methylamino-8-azabi-
cyclo[4.3.0]non-4-en-8-yl)-5-oxo-9,1-[(N-meth-
ylimino)methano]-5H-thiazolo[3,2-a]quinoline-4-
carboxylic acid 80 mg (0.248 mmol) of 7,8-difluoro-5-oxo-9,1-[(N-methylimino)methano]-5H-thiazolo[3,2-a]quinoline-4-carboxylic acid are heated under argon at 120° C. for 8 hours with 57 mg (0.375 mmol) of (1SR,2RS,6RS)-2-methylamino-8-azabicyclo[4.3.0]non-4-ene in 3 ml of DMSO. The mixture is concentrated under a high vacuum and the residue is recrystallized from ethanol and dried.
Yield: 93 mg (85% of theory)
Melting point: 281° C. Example 10

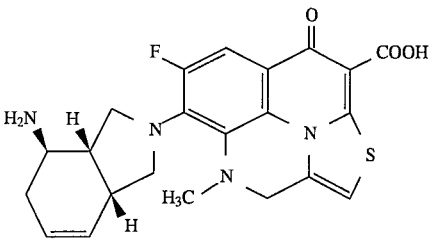

roc.

8-((1SR,2RS,6RS)-2-Amino-8-azabicyclo[4.3.0]
non-4-en-8-yl)-7-fluoro-5-oxo-9,1-[(N-methylimi-
no)methano]- 5H- thiazolo-[3,2-a]quinoline-4-car-
boxylic acid Analogously to Example 9, in the reaction with (1SR, 2RS,6RS)-2-amino-8-azabicyclo[4.3.0]non-4-ene, the title compound is obtained.
Melting point: 270° to 274° C.

We claim:
1. A 1,9-bridged thiazolo[3,2-a]quinoline derivative of the formula

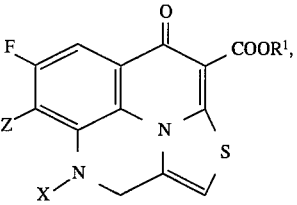

(I)

in which
$R^1$ represents hydrogen, optionally hydroxyl-, methoxy-, amino-, methylamino- or dimethylamino-substituted alkyl having 1 to 4 carbon atoms or (5-methyl-2-oxo-1,3-dioxol-4-yl)-methyl, X represents straight-chain or branched $C_1$–$C_3$-alkyl or cyclopropyl, Z represents a radical of the formula

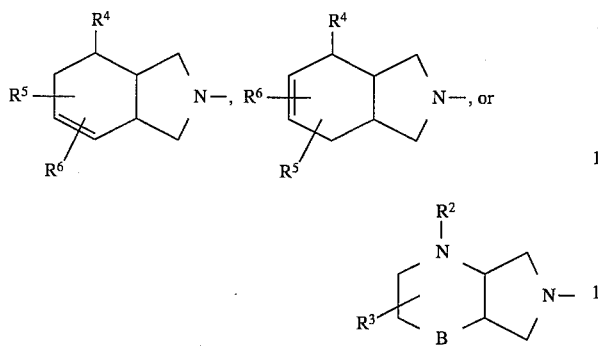

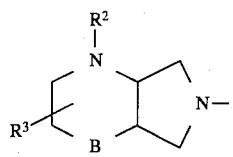

in which

R$^4$ represents hydrogen, hydroxyl, -NR$^7$R$^8$, hydroxymethyl, —CH$_2$—NR$^7$R$^8$, carboxyl, methoxycarbonyl or ethoxycarbonyl, where R$^7$represents hydrogen, optionally hydroxyl-substituted $C_1$–$C_3$-alkyl, alkoxycarbonyl having 1 to 4 carbon atoms in the alkoxy moiety or $C_1$–$C_3$-acyl, represents hydrogen or methyl, R$^5$ represents hydrogen, straight-chain or branched $C_1$–$C_3$-alkyl or cyclopropyl, R$^6$ represents hydrogen or methyl, R$^3$ represents hydrogen or methyl, R$^2$ represents hydrogen, methyl or a radical of the formula —CH=CH—COOR$^2$', —CH$_2$—CH$_2$—COOR$^2$', —CH$_2$—CO—CH$_3$, or —CH$_2$—CH$_2$—CN, wherein R$^2$ represents methyl or ethyl, B represents —CH$_2$—, O or a direct bond, in its racemate or a enantiomerically pure form or a pharmaceutically acceptable hydrate or acid addition salt thereof.

2. A process for the preparation of a 1,9-bridged thiazolo[3,2-a]quinoline derivative according to claim 1

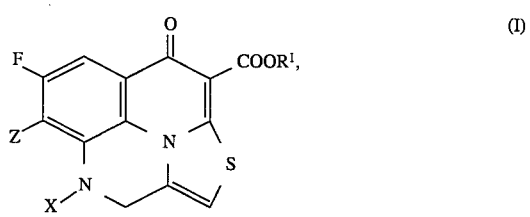

in which

R$^1$ represents hydrogen, optionally hydroxyl-, methoxy-, amino-, methylamino- or dimethylamino-substituted alkyl having 1 to 4 carbon atoms or (5-methyl-2-oxo-1,3-dioxol-4-yl)-methyl, X represents straight-chain or branched $C_1$–$C_3$-alkyl or cyclopropyl, Z represents a radical of the formula

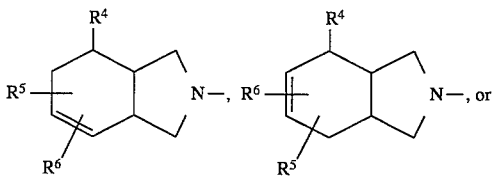

in which

R$^4$ represents hydrogen, hydroxyl, -NR$^7$R$^8$, hydroxymethyl, —CH$_2$—NR$^7$R$^8$, carboxyl, methoxycarbonyl or ethoxycarbonyl, where R$^7$represents hydrogen, optionally hydroxyl-substituted $C_1$–$C_3$-alkyl, alkoxycarbonyl having 1 to 4 carbon atoms in the alkoxy moiety or $C_1$–$C_3$-acyl, R$^8$ represents hydrogen or methyl, R$^5$ represents hydrogen, straight-chain or branched $C_1$–$C_3$-alkyl or cyclopropyl, R$^6$ represents hydrogen or methyl, R$^3$ represents hydrogen or methyl, R$^2$ represents hydrogen, methyl or a radical of the formula —CH=CH—COOR$^2$', —CH$_2$—CH$_2$—COOR$^2$', —CH$_2$—CO—CH$_3$, —CH$_2$—CH$_2$—CN, R$^2$' represents methyl or ethyl, B represents —CH$_2$—, or a direct bond, which comprises reacting a compound of the formula

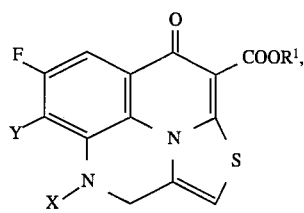

in which

R$^1$ and X have the meaning given above and

Y represents fluorine or chlorine, with a compound of the formula $$Z-T \qquad (III)$$

in which

Z has the meaning given above, optionally in the presence of acid scavengers.

3. A 1,9-bridged thiazolo[3,2-a]quinoline derivative according to claim 1, in which represents hydrogen, optionally hydroxyl-, methoxy-, amino-, methylamino- or dimethylamino-substituted alkyl having 1 to 4 carbon atoms or (5-methyl-2-oxo-1,3-dioxol-4-yl)-methyl, X represents methyl, ethyl or cyclopropyl, Z represents a radical of the formula

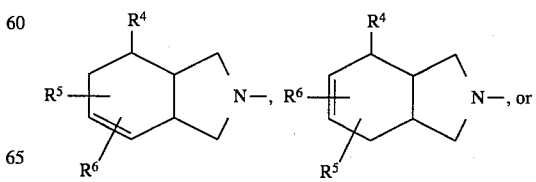

-continued

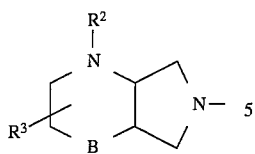

in which

R⁴ represents hydrogen, hydroxyl, -NR⁷R⁸, hydroxymethyl, —CH₂—NR⁷R⁸, where
R⁷ represents hydrogen, optionally hydroxyl-substituted C₁-C₂-alkyl, alkoxycarbonyl having 1 to 4 carbon atoms in the alkoxy moiety or C₁-C₃-acyl,
R⁸ represents hydrogen or methyl,
R⁵ represents hydrogen, straight-chain or branched C₁-C₃-alkyl or cyclopropyl,
R⁶ represents hydrogen or methyl,
R³ represents hydrogen,
R² represents hydrogen or methyl,
B represents —CH₂—, O or a direct bond, or a pharmaceutically acceptable hydrate or acid addition thereof.

4. A 1,9-bridged thiazolo[3,2-a]quinoline derivative according to claim 1, in which
R¹ represents hydrogen, methyl or ethyl,
X represents methyl or ethyl,
Z represents a radical of the formula

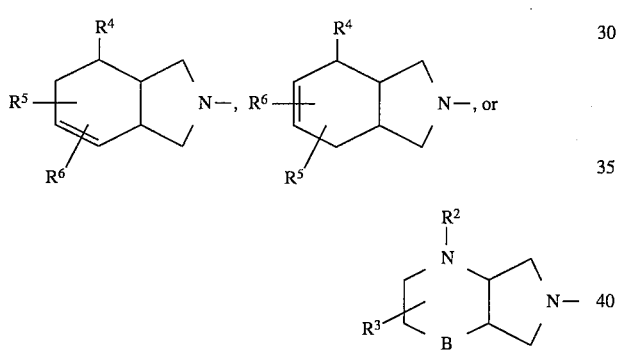

in which

R⁴ represents hydrogen, hydroxyl, -NR⁷R⁸, hydroxymethyl, or —CH₂—NR⁷R⁸, where
R⁷ represents hydrogen, methyl, alkoxycarbonyl carbonyl having 1 to 4 carbon atoms in the alkoxy moiety or C₁-C₃-acyl,
R⁸ represents hydrogen or methyl,
R⁵ represents hydrogen, straight-chain or branched C₁-C₃-alkyl or cyclopropyl,
R⁶ represents hydrogen or methyl,
R³ represents hydrogen
R² represents hydrogen or methyl,
B represents —CH₂—, O or a direct bond, or a pharmaceutically acceptable hydrate or acid addition salt, thereof.

5. The compound according to claim 1, wherein the acid addition salt is an alkali metal salt, alkaline earth metal salt, silver salt or a guanidinium salt.

6. A compound according to claim 1 wherein such compound is 7-fluoro-8-(2-methylamino-8-azabicyclo[4.3.0]non-3-en-8-yl)-5-oxo-9,1-[(N-methylimino)-methano]-5H-thiazolo-[3,2-a ]quinoline-4-carboxylic acid of the formula

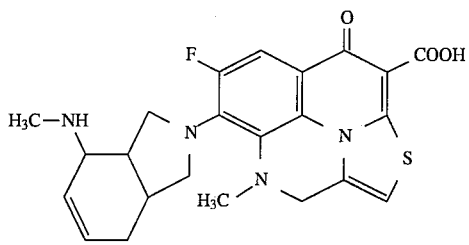

7. A compound according to claim 1 wherein such compound is 8-(2-amino-5-methyl-8-azabicyclo[4.3.0]non-3-en-8-yl)-7-fluoro-5-oxo-9,1[(N-methylimino)methano]-5H-thiazolo-[3,2-a]quinoline-4-carboxylic acid of the formula

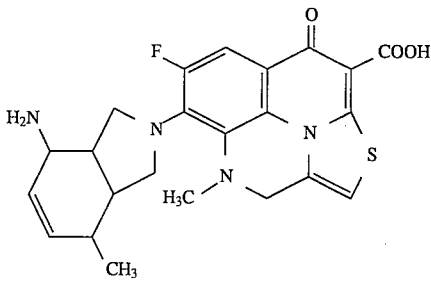

8. A compound according to claim 1 wherein such compound is 7-fluoro-8-(2-methylamonomethyl-8-azabicyclo[4.3.0]non-3-en-8-yl)-5-oxo-9,1-[(N-methylimino)methano]-5H-thiazolo-[3,2-a]quinoline-4-carboxylic acid of the formula

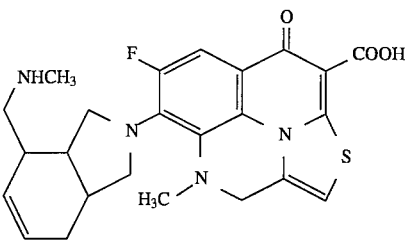

9. An antibacterial composition comprising an antibacterially effective amount of a compound, hydrate or salt thereof according to claim 1 and a diluent.

10. A method of combatting bacteria in a patient in need thereof which comprises administering to such patient an antibacterially effective amount of a compound, hydrate or salt thereof according to claim 1.

11. The method according to claim 10, wherein such compound is 7-fluoro-8-(2-methylamino-8-azabicyclo[4.3.0]non-3-en-8-yl )-5-oxo-9,1-[(N-methylimino)-methano]-5H-thiazolo-[3,2-a]quinoline-4-carboxylic acid, 8-(2-amino-5-methyl-8-azabcyclo[4.3.0]non-3-en-8-yl)-7-fluoro-5-oxo-9,1 [(N-methylimino)methano]-5H-thiazolo-[3,2-a]quinoline-4carboxylic acid, 7-fluoro-8-(2-methylamonomethyl-8-azabicyclo[4.3.0]non-3-en-8-yl)-5-oxo-9,1-[(N-methylimino)methano]-5H-thiazolo-[3,2a]quinoline-4-carboxylic, or a hydrate or salt thereof.

* * * * *

UNITED STATES PATENT AND TRADEMARK OFFICE
CERTIFICATE OF CORRECTION

PATENT NO. : 5,618,815
DATED : April 8, 1997
INVENTOR(S) : Jaetsch, et al.

It is certified that error appears in the above-indentified patent and that said Letters Patent is hereby corrected as shown below:

Col. 21, line 27    Before " represents " insert -- $R^8$ --

Col. 21, line 35    Delete " $R^2$ " and Substitute -- $R^{2'}$ --

Col. 22, line 45    Delete " Z-T " and substitute -- Z-H --

Col. 22, line 52    Before " represents " insert -- $R^1$ --

Col. 23, lines 47-48    Delete " carbonyl "

Signed and Sealed this

Twenty-second Day of July, 1997

Attest:

BRUCE LEHMAN

*Attesting Officer*    *Commissioner of Patents and Trademarks*